(12) United States Patent
Patel et al.

(10) Patent No.: US 9,861,655 B2
(45) Date of Patent: Jan. 9, 2018

(54) TOPICAL FORMULATIONS OF HEPARIN

(71) Applicant: TROIKAA PHARMACEUTICALS LIMITED, Gujarat (IN)

(72) Inventors: Ketan R. Patel, Gujarat (IN); Milan R. Patel, Gujarat (IN); Asheel K. Patel, Gujarat (IN); Prakash J. Shah, Gujarat (IN)

(73) Assignee: Troikaa Pharmaceuticals Limited, Gujarat (IN)

(*) Notice: Subject to any disclaimer, the term of this patent is extended or adjusted under 35 U.S.C. 154(b) by 0 days.

(21) Appl. No.: 15/116,060

(22) PCT Filed: Feb. 10, 2015

(86) PCT No.: PCT/IB2015/050986
§ 371 (c)(1),
(2) Date: Aug. 2, 2016

(87) PCT Pub. No.: WO2015/118512
PCT Pub. Date: Aug. 13, 2015

(65) Prior Publication Data
US 2017/0165291 A1      Jun. 15, 2017

(30) Foreign Application Priority Data
Feb. 10, 2014  (IN) ............................ 475/MUM/2014

(51) Int. Cl.
| | | |
|---|---|---|
| *A61K 31/727* | (2006.01) | |
| *A61K 9/08* | (2006.01) | |
| *A61K 47/10* | (2017.01) | |

(52) U.S. Cl.
CPC .............. *A61K 31/727* (2013.01); *A61K 9/08* (2013.01); *A61K 47/10* (2013.01)

(58) Field of Classification Search
None
See application file for complete search history.

(56) References Cited

U.S. PATENT DOCUMENTS

| | | |
|---|---|---|
| 5,958,379 A | 9/1999 | Regenold et al. |
| 2002/0032171 A1 | 3/2002 | Chen et al. |
| 2013/0102564 A1* | 4/2013 | Virno ................. A61K 9/0014 514/56 |

FOREIGN PATENT DOCUMENTS

| | | |
|---|---|---|
| EP | 0733357 B1 | 7/2002 |
| WO | 02083086 A1 | 10/2002 |
| WO | 2011138262 A1 | 11/2011 |

OTHER PUBLICATIONS

F.P. Bonina, et al., "Penetration Enhancer Effects on In Vitro Percutaneous Absorption of Heparin Sodium Salt", International Journal of Pharmaceutics, May 25, 1992, pp. 171-177, vol. 82, No. 3, Elsevier BV, NL, XP025543792.

(Continued)

*Primary Examiner* — Kevin S Orwig
*Assistant Examiner* — Barbara Frazier
(74) *Attorney, Agent, or Firm* — Baker and Hostetler LLP

(57) ABSTRACT

The present invention relates to advanced topical formulations of pharmaceutically acceptable salts of Heparin providing enhanced transdermal penetration. The present invention provides clear, non-sticky liquid formulations in which the drug is ready-for-absorption and which are suitable for administration in the form of a solution or a spray. The topical formulations of the present invention do not form flaky or gel-like film on skin surface upon topical application.

13 Claims, 3 Drawing Sheets

(56) References Cited

OTHER PUBLICATIONS

Glen L. Xiong, et al., "Effects of Penetration Enhancers on In Vitro Percutaneous Absorption of Low Molecular Weight Herparin Through Human Skin", Journal of Controlled Release, Dec. 1, 1996, pp. 289-296, vol. 42, No. 3, Elsevier, Amsterdam, NL, XP004069863.

Pankaj Karande, et al., "Enhancement of Transdermal Drug Delivery via Synergistic Action of Chemicals", Biochimica et Biophysica Acta, Nov. 1, 2009, pp. 2362-2373, vol. 1788, No. 11, Elsevier, Amsterdam, NL, XP026708909.

T. Arun Babu, et al., "Prophylactic Topical Heparin Can Prevent or Postpone Intravenous Cannula Induced Superficial Thrombophlebitis", Medical Hypotheses, 2010, pp. 857-585, vol. 74, Elsevier, NL.

R. Katzenschlager, et al., "Liposomal Heparin-Spraygel in Comparison with Subcutaneous Low Molecular Weight Heparin in Patients with Superficial Venous Thrombosis. A Randomized, Controled, Open Multicentre Study", 2003, pp. 375-378, vol. 10, No. 9.

G. Belcaro, et al., Topical Formulation of Heparin is Effective in Reducing the Symptoms of Superficial Venous Thrombosis: a Monocenter, Observer-Blind, Placebo-Controled Randomized Study, Panminerva Medica, 2011, pp. 3-11, vol. 53.

\* cited by examiner

TOPICAL FORMULATIONS OF HEPARIN

CROSS REFERENCE TO RELATED APPLICATIONS

This application is a National Stage of International Application No. PCT/IB2015/050986, filed on Feb. 10, 2015, which claims priority to Indian patent application no. 475/MUM/2014, filed on Feb. 10, 2014, the disclosures of which are incorporated by reference in their entirety.

FIELD OF THE INVENTION

The present invention relates to topical formulation of pharmaceutically acceptable salts of Heparin. The present invention more particularly relates to advanced topical formulation of heparin salts providing enhanced transdermal penetration.

BACKGROUND OF THE INVENTION

Superficial venous thrombophlebitis (SVT) is a condition of inflammation of vein caused by a thrombus formation in a vein below the skin surface resulting from an injury to vein. It is also caused due to the use of intravenous catheterization or a surgical procedure.

Infusion related superficial venous thrombophlebitis (SVT) is common in hospitalized patients who receive intravenous therapies. This localized thrombophlebitis increases pain and suffering of patients resulting in increased cost of therapy due to frequent change of venous catheter lines as well as treatment of complications of local venous thrombophlebitis. (Arun B and Sharmila V. Prophylactic topical heparin can prevent or postpone intravenous cannula induced superficial thrombophlebitis. Med Hypotheses 2010; 74: 857-858). Superficial venous thrombophlebitis may also complicate varicose veins. According to published literature, the incidence of this complication ranges between 5.6 and 44%. (Katzenschlager R, Ugurluoglu A, Hirsch M. Liposomal heparin-spraygel in comparison with subcutaneous low molecular weight heparin in patients with superficial venous thrombosis. A randomized, controlled, open multicentre study, J Kardiol 2003; 10(9): 375-378)

Heparin is used in the treatment of SVT topically as well as systemically. It belongs to a group of compounds that inhibit blood coagulation and/or the compounds that inhibit platelet aggregation. The topical use of such compounds is more convenient option than the systemic delivery. Apart from the avoidance of further complications due to systemic delivery, locally acting anticoagulants/antithrombotic agents have positive effects on the reduction in the size of thrombus (Clot) and pain/inflammation. Topical heparin formulations are also used for management of varicose veins bruises due to various types of external injuries, inflammable infiltrates and venous ulcers. (Belcaro G, Cesarone M, Dugall M, Feragalli B, Ippolito E, Corsi M et al. Topical formulation of heparin is effective in reducing the symptoms of superficial venous thrombosis: a monocenter, observer-blind, placebo-controlled randomized study. Panminerva Med 2011; 53 (Suppl. 1 to No. 3): 3-11)

Topical formulations of heparin or its pharmaceutically acceptable salts are used for the treatment of thrombophlebitis. These formulations are available in the form of viscous gels, thixotropic sprayable gels, ointments, creams or in the form of liposomal formulations, wherein the drug is incorporated in a Phospholipid bilayer. Higher dose of topical heparin formulations have advantageous therapeutic effects as compared to the lower dose formulations. Despite the use of high concentration of Heparin salt in the formulation inadequate skin penetration of the drug from the known topical formulations leads to sub-par therapeutic effects. This is evident from the longer duration of treatment required to subside the symptoms such as pain and inflammation associated with thrombophlebitis.

The dose of heparin or its variants with different molecular weights such as enoxaparin or Heparin salts such as Heparin sodium, Heparin calcium or heparinoids are mentioned in terms of International Units (IU). Topical formulations of heparin with strength ranging from 50 to 2500 IU/gm are recommended.

Heparin or its salts when used by topical route of administration are intended to provide action below the superficial skin layer. To provide adequate therapeutic benefits it is necessary that these formulations are well absorbed through the skin. Most of the topical formulations applied on the skin in the form of creams/ointments/gels/liposomes do not provide requisite penetration of the drug from the stratum corneum barrier of the skin in requisite concentration and hence, rather than providing desired therapeutic benefit, they merely work as good as a placebo. The formulations containing various ingredients such as thixotropy inducing agents although claim to provide sprayable formulations they result in the formation of a flaky film on the surface of affected area which makes such formulations unacceptable and cosmetically unpleasant for the patient.

Conventional approaches for providing topical formulations of heparin or its salt incorporate the use of lipid-like greasy ingredients or polymers or other ingredients that make them sticky and/or gel-like (highly viscous) in nature and therefore, require sufficient pressure for application of the same on the affected area and/or results in formation of a flaky or gel-like film on the skin surface. Some of the formulations also mandate potent/cytotoxic components such as DMSO which may further irritate the skin of the target area leading to patient discomfort.

All these topical formulations of Heparin or its salt use high proportion of water as the principal carrier without considering the impact of such predominantly aqueous formulations on transdermal penetration of Heparin.

Various approaches have been adopted to provide enhanced penetration of different pharmaceutically active agents especially polar active agents such as the salts of a pharmaceutically active agent. One of them is the incorporation of lipophilic penetration enhancers in the oily phase and the drug in the aqueous phase by way of formulating emulsions/microemulsions.

Further, various emulsifiers/surfactants are employed to dissolve the highly lipophilic component by formation of micelles in a system containing water or by preparing oil in water (o/w) emulsions. However, such emulsion formulations, unless well formulated, are highly unstable in nature and tend to cream due to the coalescence of lipid globules upon storage resulting in non-uniform dose distribution in a formulation. It is also important to control the globule size of the dispersed phase in such a formulation to ensure dose uniformity and stability. These emulsions are available in the form of opaque creams, lotions or translucent formulations.

Another approach is the incorporation of a phospholipid component in the formulation as an essential ingredient which engulfs the drug in solubilized state to form vesicles filled with aqueous solution of the drug, known as liposomes. However, apart from the inherent stability issues, formulation of such system is complex, highly time consuming and non-reproducible.

Further, some to the formulations also suggest the use of predominantly aqueous systems which mandates the use of specific excipients in the form of a polymer or a surfactant or one or more penetration enhancers. None of these focus on arriving at an improved carrier system which in itself is capable of providing optimum transdermal penetration even in absence of the ingredients such as surfactants or use of high proportion of penetration enhancers.

Therefore, there is an unmet need for stable topical formulations capable of providing pharmaceutically acceptable salts of heparin in a therapeutically effective amount that provide enhanced penetration of the drug and at the same time provide excellent patient compliance with pleasant feel on the skin surface as well as reduced untoward effects.

WO02083086A1 discloses topical pharmaceutical formulations used in the treatment of skin and/or mucous membrane injuries more specifically injuries related to burns. These formulations contain at least one osmolarity correcting agents.

WO2011138262 discloses topical solutions of Heparin & at least one polyoxyalkylene ester of hydroxy fatty acid in water and at least one alcohol or mixture thereof.

EP0733357B1 discloses thixotropic topical formulation with gel-like consistency containing colloidal silicates as gelifying agents which are nebulizable by a mechanical pump.

U.S. Pat. No. 5,958,379 discloses pharmaceutical composition of topically applicable substance which upon spraying on affected area forms a concentrated gel-like preparation on the skin/mucous mucous membrane surface wherein the composition contains easily evaporable alcohol(s) in the range of 5 to 40% by weight and water in the range of 50 to 90% by weight.

US2002032171 discloses pharmaceutical composition of therapeutic agents in a carrier, wherein the carrier is formed from a combination of triglyceride and at least two surfactants, at least one of which is hydrophilic. Upon dilution with an aqueous medium these formulations result in a clear aqueous dispersion of triglyceride and surfactants.

There is a need for the topical formulations of pharmaceutically acceptable salts of Heparin capable of providing safe, stable, reproducible dosage forms for a requisite amount of drug using optimum amount of water which at the same time provide enhanced transdermal penetration and are administered with ease leading to better patient compliance.

OBJECT OF THE INVENTION

The main object of the present invention is to provide formulations of pharmaceutically acceptable salts of Heparin with excellent transdermal penetration and enhanced therapeutic effectiveness when applied topically in conditions such as Superficial Venous thrombophlebitis (SVT).

Another object of the invention is to provide stable topical formulations of pharmaceutically acceptable salts of heparin in the form of a clear, non-sticky, water washable liquid formulation which is suitable for administration preferably in the form of a solution or a spray and which does not result in the formation of a flaky/gel-like film after application to the skin surface.

Another object of the invention is to provide topical formulations of pharmaceutically acceptable salts of Heparin that provide enhanced patient compliance and reduced adverse effects.

It is another object of the present invention is to provide clear, transparent, reproducible topical formulation of pharmaceutically acceptable salts of Heparin with the dose ranging from 50 to 2500 IU/ml by using optimum amount of water.

The homogeneous topical formulations of the present invention provide pharmaceutically acceptable salts of heparin in a homogeneous "ready-for-absorption" composition which does not require partitioning of the drug from one phase to the other phase of the formulation and provides rapid penetration of the drug through the skin.

The present invention provides topical formulation of pharmaceutically acceptable salts of heparin in the form of a clear transparent solution that is not only easily administered on the affected area but also provides quick and enhanced penetration of drug through skin without leaving any sticky/gel-like or flaky residues on the skin.

SUMMARY OF INVENTION

According to an aspect of the present invention there is provided topical formulations of pharmaceutically acceptable salts of Heparin comprising:
  50 to 2500 IU/ml of pharmaceutically acceptable salts of Heparin;
  less than or equal to 30% v/v of water;
  10 to 30% v/v of a lower chain alcohol; and
  a water miscible vehicle selected from a group comprising propylene glycol, glycerol, glycofurol, polyethylene glycols or any mixtures thereof.

DETAILED DESCRIPTION OF THE INVENTION

Figure 1:
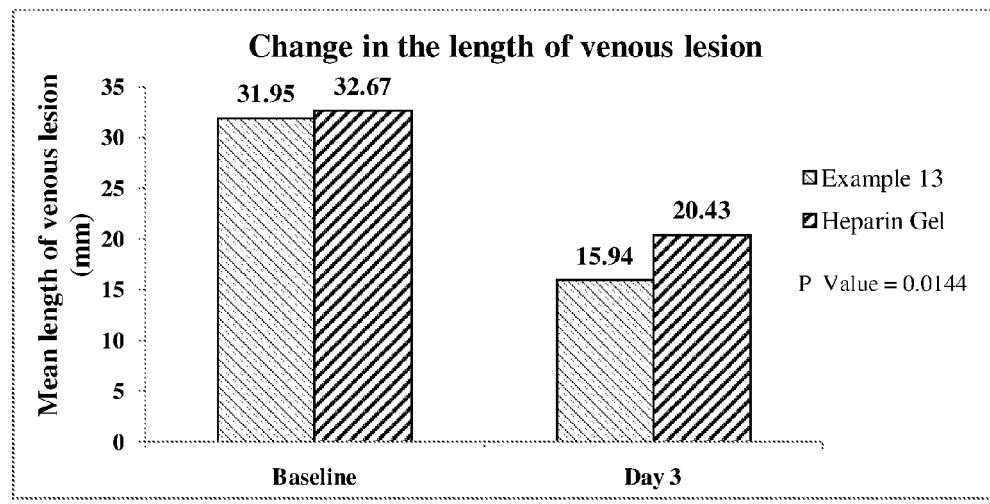
FIG. 1: Comparison of length of the venous lesion on day 3

The present invention meets the above mentioned and other needs by providing topical formulations of pharmaceutically acceptable salts of heparin in the form of a homogeneous liquid formulation with an advanced carrier system.

The inventors of the present invention surprisingly found that it is possible to prepare a clear transparent formulation of pharmaceutically acceptable salts of Heparin in an amount ranging from 50 IU/ml to 2500 IU/ml in an advanced carrier system wherein, the drug is incorporated in a formulation comprising optimum amount of water in combination with sufficient amount of water-miscible/non-aqueous carrier system and yet provide enhanced penetration of the drug across the skin.

The homogeneous formulations of present invention are in the form of clear transparent solutions which are more stable upon storage as compared to the formulations containing a dispersed phase such as vesicles, micelles or thixotropic gels which has the tendency of creaming or cracking. At the same time, the formulations of the present invention are capable of providing excellent penetration of the requisite dose of drug incorporated in the formulations.

Formulations in accordance with the present invention not only provide stable formulations of Heparin salts but also surprisingly results in the enhanced transdermal penetration and thereby provide drastic improvement in the therapeutic effect of the drug. The topical formulations of the present invention are in the form of clear homogenous solution which may be used in the form of a spray.

In the formulations of present invention, the drug is available in a uniformly solubilized state in the homogeneous formulation and the absorption of drug from the formulation is instantaneous and reproducible. These formulations advantageously are in the from of a clear transparent solution which can be applied easily to the affected area without providing pressure or leaving a sticky/gel-like or flaky residue on the skin surface and at the same time resulting in improved patient compliance when compared to relatively viscous formulations such as viscous-gels, creams, ointments, etc.

The desired viscosity of the formulation in the present invention is not more than 50 mPa·s (when measured at 25° C. by using Ostwald viscometer.). Preferably the viscosity of the formulations in the present invention is in the range to 10 to 50 mPa·s. More preferably the viscosity of the present invention is in the range of 25 to 40 mPa·s.

It was surprising that the formulations of present invention provide the abovementioned and other benefits by using an advanced carrier system with optimum amount of water and by using a selection of ingredients in proportion that are safe when applied topically and therefore minimise the adverse reactions and in turn contribute positively to the health of the patients.

The formulations in accordance with the present invention provide dose of Heparin salt in a therapeutically effective amount which can elicit desired transdermal penetration and at the same time are safe when applied topically. Preferably, the amount of pharmaceutically acceptable salts of Heparin is in the range of 50 to 2500 IU/ml.

Most surprisingly, the formulations of the present invention are capable of providing heparin salt in an amount ranging from 50 to 2500 IU/ml by using optimum amount of water in combination with a water-miscible carrier(s) as the principal vehicle and yet provide enhanced transdermal penetration.

The formulation in accordance with the present invention incorporates water in a optimum amount in combination with a carrier system or the "base" of the formulation that augments the transdermal penetration of the drug. Preferably, the amount of water incorporated in the present formulation is less than or equal to 30% v/v and more preferably less than or equal to 25% v/v. The amount of water used in the formulation of present invention is in the range of 2% to 30% v/v of the formulation. More preferably, the amount of water in the formulation of the present invention ranges from 2 to 25% v/v of the formulation. In a preferred embodiment, the amount of water used in the formulation of the present invention is less than or equal to 10% v/v of the formulation.

The penetration enhancer(s) used in accordance with the present invention are lower chain alcohol(s) with a carbon chain length ranging from C1 to C5 or mixtures thereof. Preferably, the penetration enhancers of the present invention are selected from a group comprising ethanol, isopropanol and their like, or mixtures thereof. The formulations of the present invention avoid the use of such penetration enhancers in high proportion and thereby avoid adverse effects on the skin such as dehydration and irritation of skin in case of alcohols. The said penetration enhancer(s) of the present invention is used in the range of 10 to 30% v/v of the formulation. In the preferred embodiments, the penetration enhancer of the present invention is used in the range of 10 to 20% v/v. Most preferably the penetration enhancer(s) is used in the amount of 10% v/v of the formulation.

The formulations of present invention use one or more water-miscible vehicle(s) as the principal vehicle of the topical formulations. The said water-miscible vehicle used for the formulations of the present invention can be selected from a group comprising Propylene Glycol, Glycerol, Glycofurol, Poly Ethylene Glycols (e.g. PEG400, PEG600 an the like) or mixtures thereof. The said vehicle for the topical formulations of the present invention is incorporated in an amount not less than 45% v/v preferably not less than 50% v/v of the formulation.

The formulations of the present invention use a carrier system wherein the amount of the said water-miscible vehicle (either single component or combination of multi-components) is incorporated in a proportion always higher than the proportion of water used in the present formulation.

In one of the embodiments of the present invention, the water-miscible vehicle used for the formulations of the present invention is propylene glycol either alone or in combination with one or more of Glycerol, Glycofurol, Poly Ethylene Glycols (e.g. PEG400, PEG600 an the like). Preferably, the water-miscible vehicle used in the formulations of the present invention comprises a combination of propylene glycol and Glycerol. Most preferably, the water-miscible vehicle of the formulation of the present invention comprises a combination of propylene glycol and Glycerol wherein the Glycerol is used in an amount ranging from 10 to 20% v/v of the formulation.

It is surprising to note that unlike the formulations known in the art, by use of such a carrier system in combination with the penetration enhancer the formulation of the present invention are highly stable and surprisingly provide enhanced transdermal penetration of Heparin Salt.

The formulations of the present invention may further comprise additional penetration enhancer(s). The additional penetration enhancer(s) of the present formulation can be selected from a non-limiting group of penetration enhancers known in the art such as fatty acids or fatty acid derivatives, Surfactants (Anionic, cationic or non-ionic surfactants), Azones (such as Lauracapram), Amides (such as Urea and its derivatives), Esters (such as Ethyl acetate, Octyl salicylate), Ethers (such as Dimethyl-isosorbide), Bile salts (such as sodium deoxycholate, sodium taurocholate or sodium glycocholate), Polyols or Glycol derivatives (such as Dipropylene glycol, Monoethyl ether of diethylene glycol) or complex forming agents such as (cyclodextrin or derivatives thereof) etc. The said additional penetration enhancer(s) can be used in an amount ranging from 0% to 30% v/v of the formulation.

Additionally, the formulations of the present invention may comprise ingredients known in the art to further improve or impact the acceptability/stability of the topical formulation of the present invention. Such ingredients known in the art may be selected from but are not limited to a group comprising, preservatives, stabilizers, anti-oxidants, humectants, colouring agents, pH-modifiers, buffers or perfumes or mixtures thereof.

It was observed that the formulations of present invention provide superior penetration of Heparin salt as compared to the comparative formulations comprising water as the principal carrier and non-polar solvents such as Propylene Glycol in a relatively lower amount. Further, the present formulations also provide enhanced penetration of Heparin salt as compared to the formulations available in the market (Thrombophob® Gel 200 IU).

Non-limiting examples of the formulations of the present invention in the form of a clear transparent solution are as provided below.

Example 1

| INGREDIENTS | QUANTITY |
| --- | --- |
| Heparin Sodium | 1000 IU/ml |
| Ethyl alcohol | 10% v/v |
| Water | 3.5% v/v |
| Propylene Glycol | Qs to 100% |

Viscosity of the formulation is 23 mPa·s when measured at 25° C. by using Ostwald viscometer.

Example 2

| INGREDIENTS | QUANTITY |
| --- | --- |
| Heparin Sodium | 1000 IU/ml |
| Ethyl alcohol | 10% v/v |
| Water | 3.5% v/v |
| PEG 400 | 30% v/v |
| Propylene Glycol | Qs to 100% |

Viscosity of the formulation is 35 mPa·s when measured at 25° C. by using Ostwald viscometer.

Example 3

| INGREDIENTS | QUANTITY |
| --- | --- |
| Heparin Sodium | 1000 IU/ml |
| Ethyl alcohol | 10% v/v |
| Water | 3.5% v/v |
| Glycofurol | 35% v/v |
| Propylene Glycol | Qs to 100% |

Viscosity of the formulation is 30 mPa·s when measured at 25° C. by using Ostwald viscometer.

Example 4

| INGREDIENTS | QUANTITY |
| --- | --- |
| Heparin Sodium | 1000 IU/ml |
| Ethyl alcohol | 10.0% v/v |
| Water | 3.5% v/v |
| Glycerol | 10% w/v |
| Propylene Glycol | Qs to 100% |

Viscosity of the formulation is 32 mPa·s when measured at 25° C. by using Ostwald viscometer.

Example 5

| INGREDIENTS | QUANTITY |
| --- | --- |
| Heparin Sodium | 1000 IU/ml |
| Ethyl alcohol | 10.0% v/v |
| Water | 12.5% v/v |
| Glycerol | 10% w/v |
| PEG 400 | Qs to 100% |

Viscosity of the formulation is 47.76 mPa·s when measured at 25° C. by using Ostwald viscometer.

Example 6

| INGREDIENTS | QUANTITY |
| --- | --- |
| Heparin Sodium | 1000 IU/ml |
| Ethyl alcohol | 10.0% v/v |
| Water | 20% v/v |
| Glycerol | 10% w/v |
| PEG 400 | Qs to 100% |

Viscosity of the formulation is 37.45 mPa·s when measured at 25° C. by using Ostwald viscometer.

Example 7

| INGREDIENTS | QUANTITY |
| --- | --- |
| Heparin Sodium | 1000 IU/ml |
| Ethyl alcohol | 10.0% v/v |
| Water | 3.5% v/v |
| Glycerol | 15% w/v |
| Propylene Glycol | Qs to 100% |

Viscosity of the formulation is 35 mPa·s when measured at 25° C. by using Ostwald viscometer.

Example 8

| INGREDIENTS | QUANTITY |
| --- | --- |
| Heparin Sodium | 1000 IU/ml |
| Ethyl alcohol | 12.5% v/v |
| Water | 16% v/v |
| Transcutol | 3% |
| Glycerol | 20% w/v |
| Propylene Glycol | Qs to 100% |

Viscosity of the formulation is 20 mPa·s when measured at 25° C. by using Ostwald viscometer.

| INGREDIENTS | QUANTITY |
| --- | --- |
| Heparin Sodium | 1000 IU/ml |
| Ethyl alcohol | 10.0% v/v |
| Water | 25% v/v |

-continued

| INGREDIENTS | QUANTITY |
| --- | --- |
| Glycerol | 10% w/v |
| PEG 400 | Qs to 100% |

Example 9

Viscosity of the formulation is 34.3 mPa·s when measured at 25° C. by using Ostwald viscometer.

Example 10

| INGREDIENTS | QUANTITY |
| --- | --- |
| Heparin Sodium | 2500 IU/ml |
| Ethanol | 10% v/v |
| Water | 6.5% v/v |
| Glycerol | 10% w/v |
| Propylene Glycol | Qs to 100% |

Viscosity of the formulation is 27 mPa·s when measured at 25° C. by using Ostwald viscometer.

Example 11

| INGREDIENTS | QUANTITY |
| --- | --- |
| Heparin Sodium | 2500 IU/ml |
| Ethanol | 10% v/v |
| Water | 20.0% v/v |
| Tween 80 | 0.5% w/v |
| Glycerol | 20% w/v |
| Propylene glycol | Qs to 100% |

Viscosity of the formulation is 21 mPa·s when measured at 25° C. by using Ostwald viscometer.

Example 12

| INGREDIENTS | QUANTITY |
| --- | --- |
| Heparin Sodium | 2500 IU/ml |
| Ethanol | 15% v/v |
| Water | 25.0% v/v |
| Glycerol | 15% w/v |
| PEG 400 | 20% v/v |
| Glycofurol | Qs to 100% |

Viscosity of the formulation is 30 mPa·s when measured at 25° C. by using Ostwald viscometer.

The viscosity of the formulations in the present invention is in the desired range of 10 to 50 mPa·s and the pH of the formulations is maintained nearly neutral similar to the physiological pH of the skin surface (pH 6 to 7) to avoid any irritation to the skin. If required, in order to maintain the pH of the formulations in the desired range, pH adjusting agents or buffers known in the art may also be included in the formulation. The formulations of the present invention were found to be stable on storage for duration of complete shelf life of the formulations.

Non-limiting examples of the present invention, detailed above can be prepared by the formulation processes known in the art. An outline of the process steps employed to prepare the formulations of the present invention comprises:
1. Desired amount of Heparin salt and other hydrophilic excipients (if used) are dissolved in water.
2. The solution resulting from step 1 is mixed with a part of water-miscible carrier system.
3. Hydrophobic ingredients such as preservatives etc. (if used) are solubilised in the penetration enhancer of present invention.
4. The solution resulting from step 2 above is mixed with the solution resulting from the step 3 above.
5. Auxiliary ingredients such as the pH modifiers (if any) are added to the mixture obtained at Step 4 above.
6. The final volume of the formulation is made-up using sufficient quantity of the water-miscible carrier system.

Further, in order to study the effect of the change in the proportion of water used in the present formulations and compare the same with the formulations containing water in a proportion higher than the water-miscible vehicle, formulations with the following formula were prepared and tested for in vitro transdermal penetration of Heparin Salt.

TABLE 1

Formulations for In Vitro Transdermal penetration studies:

| | QUANTITY | | | | | |
| --- | --- | --- | --- | --- | --- | --- |
| INGREDIENTS | Example 13 | Example 14 | Example 15 | Example 16 (Comparative Example) | Example 17 (Comparative Example) | Example 18 (Comparative Example) |
| Heparin Sodium | 1000 IU/ml | 1000 IU/ml | 1000 IU/ml | 1000 IU/ml | 1000 IU/ml | 1000 IU/ml |
| Ethyl alcohol | 10% v/v | 10% v/v | 10% v/v | 10% v/v | 10% v/v | 10% v/v |
| Glycerol | 15% w/v | 15% w/v | 15% w/v | 15% w/v | 15% w/v | 15% w/v |
| Methyl Paraben | 0.15% w/v | 0.15% w/v | 0.15% w/v | 0.15% w/v | 0.15% w/v | 0.15% w/v |
| Propyl Paraben | 0.05% w/v | 0.05% w/v | 0.05% w/v | 0.05% w/v | 0.05% w/v | 0.05% w/v |
| Water | 3.5% v/v | 10% v/v | 25% v/v | 35% v/v | 50% v/v | Qs to 100% |
| Propylene Glycol | Qs to 100% | Qs to 100% | Qs to 100% | Qs to 100% | Qs to 100% | 110% v/v |

The in vitro transdermal penetration of Heparin Salt was compared in the formulations of the present invention (Example 13, 14, 15), with the comparative formulations (Example 16, 17, 18) and the formulations available in the market (Thrombophob gel, Zydus) through Franz-diffusion studies.

APPARATUS: Franz Diffusion Cell Assembly (PermeGear, USA) containing six station vertical cell stirrer and a black anodized aluminum cell holder with the specification of 9 mm inside diameter of receptor chamber, 5 ml volume of receptor chamber and 0.64 $cm^2$ of membrane surface area was used for the present study.

PERMEABILITY STUDY: Permeability study was carried out with Nylon membrane placed between donor and receptor chambers of Franz diffusion cell. HPLC grade water was filled in receptor chamber and continuously stirred at 500 rpm throughout the experiment using built in magnetic stirrer. The temperature of HPLC grade water in receptor chamber was maintained at 37° C. by circulating water in the jacket around it. Measured quantity of Heparin formulations were placed in donor chamber in duplicate, as given below in the table, after the temperature of HPLC grade water in receptor chamber reached equilibrium (37° C.). The samples (0.5 mL aliquots) were withdrawn at predefined intervals up to 6 hours from the sampling port of receptor chamber. Equal volume of HPLC grade water, maintained at 37° C. was used to replace the loss in volume of the receptor chamber immediately after sampling. Collected samples were analyzed within 24 hours by HPLC.

RESULTS: The levels of Heparin salt in receptor chamber was measured with time and the average values (n=2) were used to determine Flux, Permeability coefficient and other parameters as mentioned in the table below (Table 2):

TABLE 2

In vitro Permeability results

| Formulation | Permeability Parameters | | |
|---|---|---|---|
| | Flux ($\mu g/cm^2/hr$) | Permeability Coefficient (Kp) | % Dose Penetrated At 6 Hour |
| Example 13 | 127.3 | 0.1273 | 93.71 |
| Example 14 | 135 | 0.135 | 92% |
| Example 15 | 141.3 | 0.1413 | 90.19 |
| Example 16 | 102.4 | 0.1024 | 72.97 |
| Example 17 | 97 | 0.097 | 66.08 |
| Example 18 | 79.51 | 0.07951 | 58.84 |
| Thrombophob Gel | 0 | — | — |
| | (The amount of Heparin sodium in the sample was below the detection limit) | | |

The results of Franz-diffusion studies clearly show that the penetration (flux) of Heparin Sodium is significantly higher from the formulations of the present invention as compared to the formulation using relatively higher amount of water (Example 16, 17, 18). It was surprising that when the amount of water used in the topical formulation of Heparin sodium is increased beyond a range, the penetration of Heparin sodium reduces drastically. This is further established from the fact that the penetration of Heparin Sodium from the present formulations (Example 13 to 15) is drastically higher than the marketed Heparin Sodium formulation (Thrombophob Gel) which uses water as the principal carrier system.

In order to validate the above outcome of the in vitro studies, a randomized, open label, comparative clinical study was conducted to compare the safety and efficacy of topical solutions of the present invention (Example 13), with Heparin gel formulations available in the market (Thrombophob Gel) for the management of post infusion superficial thrombophlebitis.

This prospective, randomized, two arm, open label, active controlled phase III clinical study was conducted at six different hospitals across India. Patients of either sex aged between 18-60 years, having early Grade 2-4 phlebitis (medium or advanced stage of superficial thrombophlebitis) based on phlebitis scale as per "*Standards for Infusion Therapy*" by Royal College of Nursing IV Therapy Forum July 2003; were included in the study. Total 202 patients were enrolled and randomized to either receive Heparin formulations of the present invention (Example 13) (n=100) or the Heparin gel (n=102). The study medications were applied in sufficient amount to cover the phlebitis lesion 3 times daily (morning, noon and evening) until healing or for maximum of 7 consecutive days.

Primary efficacy endpoints were, change in length of the venous lesion on day 3, change in the grade of the lesion on day 3, proportion of patients with complete healing on day 3 and 7; while secondary efficacy endpoints included local symptoms on day 3, and global assessment by patients and investigator at the end of study. Safety endpoints included occurrence of local or systemic adverse events with study treatments. Length of venous lesion in millimeter was measured using pre calibrated stainless steel scale and grade of the lesion was noted using Phlebitis Scale before the start of study (at baseline) and on day 3 after initiation of the treatment. Phlebitis scale was assessed on a 5 grade scale detailed below: (Table 3)

TABLE 3

Phlebitis scale as per standard for infusion therapy

| Grades of phlebitis | Indications |
|---|---|
| Grade 0 | No sign of phlebitis |
| Grade 1 | Possibly the first sign of phlebitis |
| Grade 2 | Early sign of phlebitis |
| Grade 3 | Medium stage phlebitis |
| Grade 4 | Advance stage of phlebitis or stage of thrombophlebitis |
| Grade 5 | Advanced stage of thrombophlebitis |

Note:
Grades are defined as per the Phlebitis scale according to the Standards for Infusion Therapy, by Royal College of Nursing IV Therapy Forum, July 2003

On the basis of this scale, proportion of patients with complete healing (Grade 0 as per phlebitis scale) was noted on day 3 and 7. Local symptoms like pain, tenderness, redness, raised local temperature and venous indurations were assessed on 4 point severity scale (0—None, 1—Light, 2—Moderate, 3—Severe) at baseline and on day 3.

The data was obtained from a total of 202 patients and were subjected to statistical analysis. Demography (age, gender, height and weight) and baseline characteristics (mean length of the venous lesion, local symptoms, and grade of phlebitis) were comparable between both the treatment groups (Table 4). All the enrolled patients had unilateral superficial thrombophlebitis on upper limb.

TABLE 4

Demographic and baseline characteristics

| Characteristics | Heparin formulations of present invention (Example 13) (N = 100) | Heparin Gel (N = 102) | p value |
|---|---|---|---|
| Age (Years) [mean ± SD] | 41.45 ± 12.29 | 38.22 ± 13.59 | 0.079 |
| Weight (kg) [mean ± SD] | 64.20 ± 12.41 | 63.24 ± 13.47 | 0.601 |
| Height (cm) [mean ± SD] | 161.47 ± 07.39 | 160.33 ± 08.15 | 0.302 |
| Gender | | | |
| Male (n) | 60 | 57 | 0.553 |
| Female (n) | 40 | 45 | |
| Length of the venous lesion (mm) [mean ± SD] | 31.95 ± 14.98 | 32.67 ± 17.16 | 0.7509 |
| Local symptoms [mean ± SD] | | | |
| Pain | 01.88 ± 00.57 | 01.88 ± 00.69 | 1.000 |
| Tenderness | 01.90 ± 00.59 | 01.87 ± 00.71 | 0.744 |
| Redness | 01.06 ± 00.69 | 01.12 ± 00.69 | 0.537 |
| Local temperature | 00.91 ± 00.67 | 00.80 ± 00.70 | 0.255 |
| Venous induration | 00.71 ± 00.81 | 00.75 ± 00.74 | 0.715 |
| Grade of phlebitis (N) | | | |
| Early stage (Grade 2) | 56 | 52 | 0.7634 |
| Medium stage (Grade 3) | 35 | 39 | |
| Advanced stage (Grade 4) | 09 | 11 | |

Values are expressed in Mean ± SD for age, weight, height, length of venous lesion and local symptoms; and absolute numbers for gender and grade of phlebitis, N = number of patients.

Primary Efficacy End-Points:
1. Change in Length of the Venous Lesion:
    A significantly higher reduction in length of venous lesion from baseline was observed in patients treated with the Heparin formulations of present invention (Example 13) on day 3, as compared to patients treated with heparin gel (p=0.0144). (See FIG. 1)

Figure 2A:
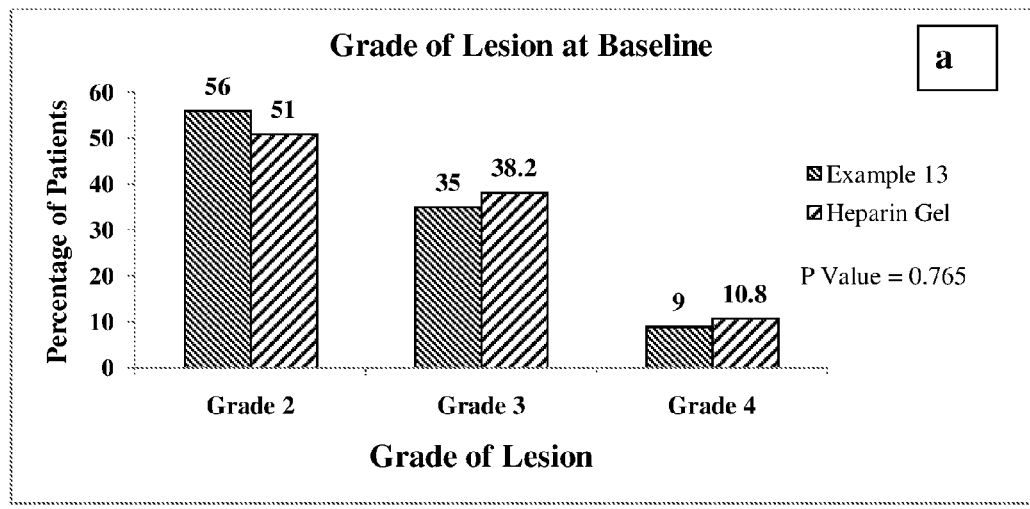
FIG. 2: Change in the grade of venous lesion at baseline (a) and at day 3 (b)
Figure 2B:
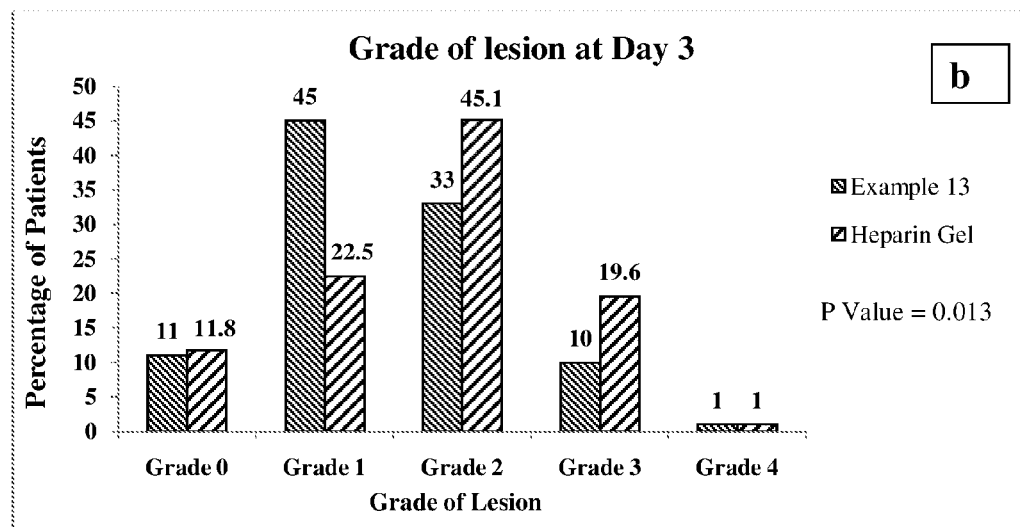

2. Change in the Grade of Venous Lesion:
    Grade of venous lesion was comparable between both the treatment groups at baseline (p=0.7634), however a significant fall in percentage of patients with grade 2 & 3 was reported in patients treated with Heparin formulations of present invention (example 13) as compared to heparin gel (p=0.0133) (See FIGS. 2 (a) & (b)).

Figure 3:
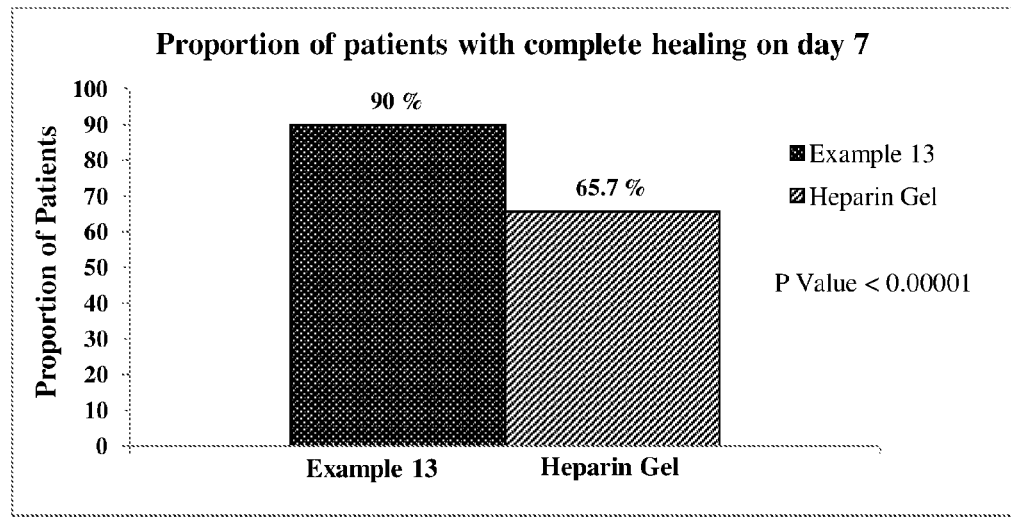
FIG. 3: Proportion of patients with complete healing on day 7

3. Proportion of Patients with Complete Healing:
    In the Heparin formulations of present invention (example 13) treatment group, 90% of the patient achieved complete resolution of the lesion on day 7, this was significantly higher as compared to 65.7% of the patients treated with heparin gel. (p<0.00001) (FIG. 3)

Secondary Efficacy End Points:
1. Changes in Local Symptoms from Baseline:
    The local symptoms were comparable at baseline in both the treatment groups. There was significant fall in tenderness and raised local temperature as compared to baseline in patients treated with Heparin formulations of present invention (Example 13) as compared to heparin gel (Table 5).

TABLE 5

Changes in local symptoms score from baseline on day 3

| Symptoms | Heparin formulations of present invention (example 13) (N = 100) | | | Heparin gel (N = 102) | | | p value |
|---|---|---|---|---|---|---|---|
| | Baseline score | Day 3 score | Change in the score | Baseline score | Day 3 score | Change in score | |
| Pain | 1.88 ± 0.57 | 1.11 ± 0.67 | 0.77 ± 00.68 | 1.88 ± 0.69 | 1.27 ± 0.75 | 0.61 ± 00.62 | 0.082 |
| Tenderness | 1.90 ± 0.59 | 0.99 ± 0.59 | 0.91 ± 00.65 | 1.87 ± 0.71 | 1.18 ± 0.79 | 0.69 ± 00.67 | 0.019# |
| Redness | 1.06 ± 0.69 | 0.40 ± 0.491 | 0.66 ± 00.71 | 1.12 ± 0.69 | 0.52 ± 0.56 | 0.60 ± 00.69 | 0.543 |
| Raised Local temperature | 0.91 ± 0.67 | 0.27 ± 0.45 | 0.64 ± 00.66 | 0.80 ± 0.70 | 0.38 ± 0.55 | 0.42 ± 00.60 | 0.014# |
| Venous induration | 0.71 ± 0.81 | 0.29 ± 0.46 | 0.42 ± 00.65 | 0.75 ± 0.74 | 0.35 ± 0.54 | 0.40 ± 00.68 | 0.831 |

Values are expressed in Mean ± SD,

N = number of patients.

Statistically significant

2. Patient's and Physician's Global Assessment

Figure 4A:
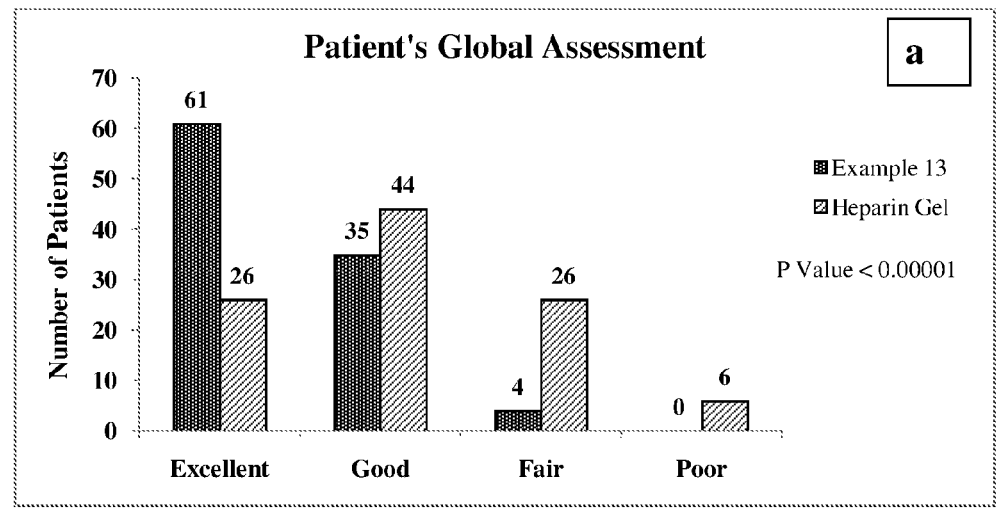
FIG. 4: Patients (a) and Physicians (b) global assessment for Heparin formulations of present invention (Example 13) and marketed Heparin gel
Figure 4B:
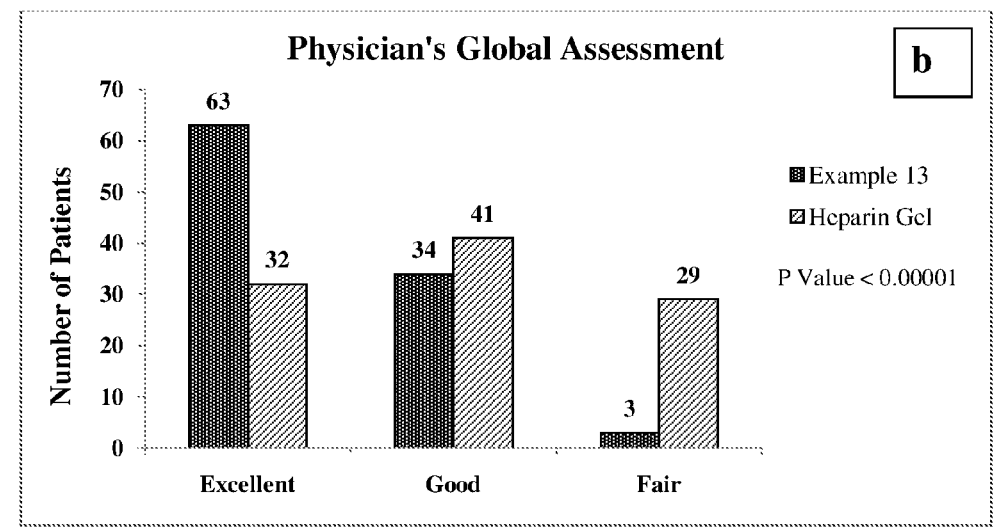

Heparin formulations of present invention (example 13) was rated Excellent-Good in most of the cases by patients (p<0.00001) and physicians (p<0.00001) (See FIGS. 4 (a) and (b)).

Safety endpoints: No cases of any expected or unexpected, local as well as systemic adverse events were reported/observed during study. No case of any abnormality in the vital data as well as in physical examination was found during study.

Discussion: The study revealed that the formulation of the present invention was found to be more effective than heparin gel as the said formulations significantly reduced the length of venous lesion. Also present formulation was found to have an excellent clinical response in term of healing as 90% of the patients experienced complete resolution of the lesion and local symptoms compared to 65.7% of the patients treated with heparin gel. These favourable results may be attributed to the higher penetration of heparin through the skin achieved by the formulations of the present invention. Further, more number of patients who were treated with the formulations of the present invention experienced significantly better improvement in grades of venous lesion from baseline phlebitis as compared to Heparin gel.

In our study, no case of any adverse events was recorded which suggests that, while improving the efficacy of heparin through quick penetrating solutions of the present invention, safety of the patients was not vitiated.

Based upon the overall efficacy and safety of both the study drugs, patients and investigator global assessment was more favourable towards heparin formulations of present invention (example 13) than heparin gel. Further, greater improvement in efficacy of heparin with similar safety profile may have contributed to the higher preference of heparin formulations of present invention (example 13).

CONCLUSION

The Heparin formulation of present invention (Example 13) was found to be more effective in treatment of post infusion superficial thrombophlebitis with similar safety profile to marketed heparin gel. Hands free usage of Heparin formulations of present invention (example 13) would facilitate ease of application and improve compliance of patients as well as nursing staff. Therefore, heparin formulations of present invention (example 13) can be a better and more convenient alternative in the management of post infusion superficial thrombophlebitis.

The results of the clinical study show that formulations of the present invention provide quick and comprehensive penetration through the stratum corneum to deliver higher amounts of heparin sodium in the underlying tissue. These formulations achieve higher penetration with minimal systemic exposure. Formulations of the present invention are safe and effective for the management of Infusion related thrombophlebitis. The formulations of present invention provide better improvement in pain at the affected site and reduction of lesion size and grade. Moreover the formulations can be provided in metered dose spray container, which is convenient to use, hence further improving the patient compliance.

In the above disclosure, it is understood that terms such as "a", "an", "the", and like are words used for convenience and are not to be constructed as limiting terms. Although the present invention has been described in considerable detail with reference to certain preferred embodiments thereof, other versions are possible. Moreover, it will be understood that the illustrations are for the purpose describing exemplary embodiment of the invention and the same do not limit the scope of the present invention.

We claim:

1. A topical formulation of pharmaceutically acceptable salts of Heparin comprising:
   50 to 2500 IU/ml of pharmaceutically acceptable salts of Heparin;
   less than or equal to 30% v/v of water;
   10 to 30% v/v of a lower chain alcohol; and
   greater than 45% v/v of a water miscible vehicle selected from the group consisting of propylene glycol, glycerol, glycofurol, polyethylene glycol and mixtures thereof.

2. The topical formulation of pharmaceutically acceptable salts of Heparin as claimed in claim 1, wherein the amount of water is less than or equal to 25% v/v of the formulation.

3. The topical formulation of pharmaceutically acceptable salts of Heparin as claimed in claim 1, wherein the amount of lower chain alcohol is in the range of 10 to 20% v/v of the formulation.

4. The topical formulation of pharmaceutically acceptable salts of Heparin as claimed in claim 3, wherein the lower chain alcohol is selected from alcohol(s) with a carbon chain length ranging from C1 to C5 or mixtures thereof.

5. The topical formulation of pharmaceutically acceptable salts of Heparin as claimed in claim 1, wherein the water miscible vehicle is propylene glycol.

6. The topical formulation of pharmaceutically acceptable salts of Heparin as claimed in claim 1, wherein the water miscible vehicle is a combination of propylene glycol and glycerol.

7. The topical formulation of pharmaceutically acceptable salts of Heparin as claimed in claim 1, wherein the amount of water is less than the amount of water miscible vehicle of the formulation.

8. The topical formulation of pharmaceutically acceptable salts of Heparin as claimed in claim 1, wherein the viscosity of the formulations is in the range of 10 to 50 mPa·s, when measured at 25° C. by using Ostwald viscometer.

9. The topical formulation of pharmaceutically acceptable salts of Heparin as claimed in claim 1, further comprising one or more additional penetration enhancers.

10. The topical formulation of pharmaceutically acceptable salts of Heparin as claimed in claim 9, wherein the one or more additional penetration enhancers is selected from the group consisting of fatty acids, surfactants, azones, amides, esters, ethers, bile salts, polyols, complex forming agents and mixtures thereof.

11. The topical formulation of pharmaceutically acceptable salts of Heparin as claimed in claim 1, further comprising a pharmaceutically acceptable excipient selected from the group consisting of preservatives, stabilizers, antioxidants, humectants, colouring agents or perfumes, and mixtures thereof.

12. The topical formulation of pharmaceutically acceptable salts of Heparin as claimed in claim 1, wherein the formulations are in the form of solution.

13. The topical formulation of pharmaceutically acceptable salts of Heparin as claimed in claim 8, wherein the viscosity of the formulations is in the range of 25 to 40 mPa·s.

* * * * *